United States Patent
Engber et al.

(12)

(10) Patent No.: US 6,184,217 B1
(45) Date of Patent: Feb. 6, 2001

(54) USE OF K-252A DERIVATIVE

(75) Inventors: Thomas M Engber, Berwyn; Forrest A. Haun, Wyncote, both of PA (US); Michael S. Saporito, Westmont, NJ (US); Lisa D. Aimone, Reading; Matthew S. Miller, Newtown, both of PA (US); Ernest Knight, Jr., Hilton Head Island, SC (US)

(73) Assignee: Cephalon, Inc., West Chester, PA (US)

( * ) Notice: Under 35 U.S.C. 154(b), the term of this patent shall be extended for 0 days.

(21) Appl. No.: 08/881,679

(22) Filed: Jun. 24, 1997

Related U.S. Application Data (60) Provisional application No. 60/020,406, filed on Jun. 25, 1996.

(51) Int. Cl.$^7$ .................. A61K 31/55; A61K 31/553; A61K 31/554

(52) U.S. Cl. .................................................. 514/211.01

(58) Field of Search .............................. 514/211, 211.01

(56) References Cited

U.S. PATENT DOCUMENTS

| | | |
|---|---|---|
| 4,554,402 | 11/1985 | Hawkins et al. . |
| 4,735,939 | 4/1988 | McCoy et al. . |
| 4,816,450 | 3/1989 | Bell et al. . |
| 4,877,776 | * 10/1989 | Murakata et al. ............ 514/211 |
| 4,923,986 | 5/1990 | Murakata et al. . |
| 5,043,335 | 8/1991 | Kleinschroth et al. . |
| 5,093,330 | 3/1992 | Caravatti et al. . |
| 5,344,926 | 9/1994 | Murakata et al. . |
| 5,461,145 | 10/1995 | Kudo et al. . |
| 5,516,771 | 5/1996 | Dionne et al. . |
| 5,621,100 | 4/1997 | Lewis et al. . |

FOREIGN PATENT DOCUMENTS

| | | |
|---|---|---|
| 17571/88 | 12/1988 | (AT) . |
| 0 238 011 A2 | 9/1987 | (EP) . |
| 0 296 110 A3 | 12/1988 | (EP) . |
| 0 323 171 A3 | 7/1989 | (EP) . |
| 0 370 236 A1 | 5/1990 | (EP) . |
| 0 558 962 A1 | 9/1993 | (EP) . |
| 62-120388 | 6/1987 | (JP) . |
| 62-155284 | 7/1987 | (JP) . |
| 62-155285 | 7/1987 | (JP) . |
| 36-295589 | 12/1988 | (JP) . |
| 63-295588 | 12/1988 | (JP) . |
| 5086068 | 4/1993 | (JP) . |
| 5247055 | 9/1993 | (JP) . |
| 6073063 | 3/1994 | (JP) . |
| WO 89/07105 | 9/1984 | (WO) . |
| WO 88/07045 | 9/1988 | (WO) . |
| WO 91/09034 | 6/1991 | (WO) . |
| WO 93/08809 | 5/1993 | (WO) . |
| WO 94/02488 | 2/1994 | (WO) . |
| WO 95/00520 | 1/1995 | (WO) . |
| WO 95/22331 | 8/1995 | (WO) . |

OTHER PUBLICATIONS

Abe et al., "Arachidonic Acid Metabolism in Ischemic Neuronal Damage," *Annals of the New York Academy of Sciences* 559:259–268 (1989).

Borasio, "Differential effects of the protein kinase inhibitor K–252a on the in vitro survival of chick embryonic neurons," *Neuroscience Letters* 108:207–212 (1990).

Bozyczko–Coyne et al., "A rapid fluorometric assay to measure neuronal survival in vivo," *Journal of Neuroscience Methods* 50:205–216 (1993).

Tischler et al., "A Protein Kinase Inhibitor, Staurosporine, Mimics Nerve Growth Factor Induction of Neurotensin/ Neuromedin N Gene Expression," *The Journal of Biological Chemistry* 266:1141–1146 (1991).

Vitullo, Press Release "Cephalon and Kyowa Hakko Co., Ltd. Announce Collaboration," Jun. 2, 1992.

Wolf et al., "The Protein Kinase Inhibitor Staurosporine, Like Phorbol Esters, Induces the Association of Protein Kinase C With Membranes," *Biochem. and Biophys. Research Communications* 154:1273–1279 (1988).

Wenk, G. et al., "Nucleus basalis magnocellularis: optimal coordinates for selective reduction of choline acetyltransferase in frontal neocortex by ibotenic acid injections," *Exp Brain Res.* 56:335–340 (1984).

Chiu, A. et al., "A Motor Neuron–Specific Epitope and the Low Affinity Nerve Growth Factor Receptor Display . . . Development, Axotomy, and Regeneration," *Journal of Comparative Neurology* 328:351–363 (1993).

Chu–Wang et al., "Cell Death of Motoneurons in the Chick Embryo Spinal Cord," *J. Comp. Neur.*, 177:33–58, 1992.

Davis et al., "Inhibitors of Protein Kinase C.1$^1$ 2,3–Bisarylmaleimides," *J. Med. Chem.* 35:177–184, 1992.

Davis et al., "Potent Selective Inhibitors of Protein Kinase C," *FEBS Letters* 259:61–63 (1989).

(List continued on next page.)

*Primary Examiner*—Jerome D. Goldberg
(74) *Attorney, Agent, or Firm*—Woodcock Washburn Kurtz Mackiewicz & Norris LLP (57) ABSTRACT

Disclosed herein are therapeutic methologies utilizing a ring substituted derivative of the indolocarbazole K-252a, the derivative represented by the formula:

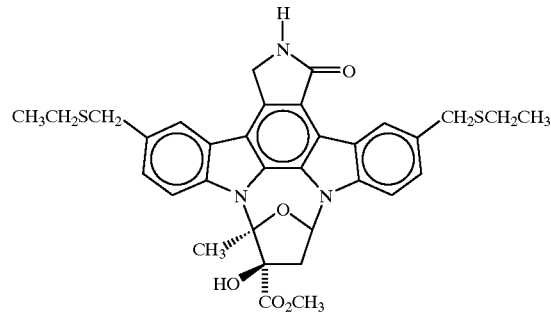

2 Claims, 3 Drawing Sheets

OTHER PUBLICATIONS

Dunnett, S. et al., "The basal forebrain—cortical cholinergic system: interpreting the functional consequences of excitotixic lesions," *TINS* 14:494–501 (1991).

Fibiger, H., "Cholinergic mechanisms in learning, memory and dementia: a review of recent evidence," *TINS* 14:220–223 (1991).

Glicksman, M. et al., "K–252a and Staurosporine Promote Choline Acetyltransferase Activity in Rat Spinal Cord Cultures," *Journal of Neurochemistry* 61:210–221 (1993).

Glicksman, M., "K–252a Molecules as Promoters . . . ", Third Int. Conference on Nerve Growth Factor (NGF) and related molecule, Chateau Lake Louise, Lake Louise, Alberta, Apr. 26–May 1, 1994.

Glicksman, M. et al., "K–252a Promotes Survival of Striatal Neurons in Culture," Society of Neuroscience Abstracts 19:680 (1993).

Hamburger, "Cell Death in the Development of the Lateral Motor Column of the Chick Embryo," *J. Comp. Neur* 160:535–546 (1975).

Hara et al., "Staurosporine, a Novel Protein Kinase C Inhibitor, Prevents Postischemic Neuronal Damage in the Gerbil and Rat," *Journal of Cerebral Blood Flow and Metabolism* 10:646–653 (1990).

Hashimoto et al., "Staurosporine–induced Neurite Outgrowth in PC12h Cells," *Experimental Cell Research* 184:351–359 (1989).

Hashimoto, "K–252a, a Potent Protein Kinase Inhibitor, Blocks Nerve Growth Factor–induced Neurite Outgrowth and Changes in the Phosphorylation of Proteins in PC12h Cells," *J. Cell Biology* 107:1531–1539, 1990.

Kase et al., "K–252a, A Protein Inhibitor of Protein Kinase C From Microbial Origin," *The Journal of Antibiotics* 39:1059–1065 (1986).

Kiyoto et al., "Staurosporine, a Potent Protein Kinase . . . Caused Ornithine Decarboxylase Induction in Isolated Mouse Epidermal Cells," *Biochem. and Biophys. Research Communications* 148:740–746 (1987).

Knüsel et al., "K–252b Selectively Potentiates Cellular Actions and trk Tyrosine Phosphorylation Mediated by Neurotrophin–3", *Journal of Neurochemistry* 59:715–722 (1992).

Knüsel et al., "K–252b Is a Selective and Nontoxic Inhibitor of Nerve Growth Factor Action on Cultured Brain Neurons," *Journal of Neurochemistry* 57:955–962 (1991).

Koizumi et al., "K–252a: A Specific Inhibitor of the Action of Nerve Growth Factor on PC12 Cells," *The Journal of Neuroscience* 8:715–721 (1988).

Lazarovici et al., "K–252a Inhibits the Increase in c–fos Transcription and the Increase in Intracellular Calcium Produced by Nerve Growth Factor in PC12 Cells," *Journal of Neuroscience Research* 23:1–8 (1989).

McManamann, J. et al., "Rescue of Notoneurons from Cell Death by a Purified Skeletal Muscle Polypeptide: Effects of the ChAT Development Factor, CDF," *Neuron* 4:891–898 (1990).

Matsuda et al., "The Effect of K–252a, A Potent Microbial Inhibitor of Protein Kinase, on Activated Cyclic Nucleotide Phosphodiesterase," *Biochem J.* 256:75–80 (1988).

Moody et al., "Synthesis of the Staurosporine Aglycon", *J. Org. Chem.* 57:2105–2114 (1992).

Morioka et al., "Staurosporine–induced Differentiation in a Human Neuroblastoma Cell Line, NB–1," *Agric. Biol. Chem.* 49:1959–1963 (1985).

Nabeshima et al., "Staurosporine, a protein kinase inhibitor, attenuates basal forebrain–lesion–induced amnesia and cholinergic neuronal deficit," *Neuroscience Letters* 122:13–16 (1991).

Nabeshima et al., "Staurosporine Facilitates Recovery from the Basal Forebrain–Lesion–Induced . . . Cholinergic Neuron in Rats," *The Journal of Pharmacology and Experimental Therapeutics* 257:562–566 (1991).

Nakadate et al., "Comparison of Protein Kinase C Functional Assays to Clarify Mechanisms of Inhibitor Action," *Biochemical Pharmacology* 37:1541–1545 (1988).

Nakanishi et al., "K–252b, c and d, Potent Inhibitors of Protein Kinase C From Microbial Origin," *The Journal of Antibiotics* 39:1066–1071 (1986).

Ohno et al., "Effect of Staurosporine, a Protein Kinase C Inhibitor, on Impairment of Working Memory in Rats Exposed to Cerebral Ischemia," *European Journal of Pharmacology* 204:113–116 (1991).

Olton, D. et al., "Dementia: Animal Models of the Cognitive Impairments . . . Cholinergic System," *Psychopharmacology: The Third Generation of Progerss*, Raven Press, NY (1987).

Oppenheim, R. et al., "Reduction of Naturally Occurring Motoneuron Death in Vivo by a Target–Derived Neurotrophic Factor," *Science* 240:919–921 (1988).

Oppenheim, "The Absence of Significant Postnatal Motoneuron Death in the Brachial and Lumbar Spinal Cord of the Rat," *Journal of Comparative Neurology*, 246:281–286 (1986).

Oppenheim, R. et al., "Cell Death of Motoneurons in the Chick Embryo Spinal Cord. VI. Reduction of Naturally Occurring Cell Death . . . Terni by Nerve Growth Factor," *Journal of Comparative Neurology*, 210:174–189 (1982).

Rasouly et al., "Staurosporine–Induced Neurite Outgrowth in PC12–Cells is Independent of Protein Kinase–C Inhibition," *Molecular Pharmacology* 42:35–43 (1991).

Sako et al., "Contrasting Actions of Staurosporine, a Protein Kinase C Inhibitor, on Human Neurophils and Primary Mouse Epidermal Cells," *Cancer Research* 48:4646–4650 (1988).

Shea et al., "Staurosporine–induced Morphological Differentiation of Human Neuroblastoma Cells," *Cell Biology International Reports* 15:161–167 (1991).

Shepherd, "The Synaptic Organization of the Brain" Second Edition, pp. 308–314 (Oxford University Press, New York, 1979).

Siman et al., "Excitatory Amino Acids Activate Calpain I and Induce Structural Protein Breakdown in Vivo," *Neuron* 1:279–287 (1988).

Slack et al., "Effects or Retinoic Acid and Staurosporine on the Protein Kinase C Activity and the Morphology of Two Related Human Neuroblastoma Cell Lines" *Biochemica et Biophysica Acta* 1053:89–96 (1990).

Smith, G., "Animal models of Alzheimer's disease: experimental cholinergic denervation," *Brain Research Reviews* 13:103–118 (1988).

Smith et al., "Effects of a Protein Kinase C Inhibitor, K–252a, on Human Polymorphonuclear Neutrophil Responsiveness," *Biochem. and Biophys. Research Communications* 152:1497–1503 (1988).

Steglich et al., "Indole Pigments from the Fruiting Bodies of the Slime Mold *Arcyria denudata*," Agnew. Chem. Int. Ed. Engl. 19:459–460 (1980).

Knüsel et al., "K–252 Compounds: Modulators of Neurotrophin Signal Transduction", Journal of Neurochemistry 59:1987–1996, 1992.

Beal et al., "Alzheimer's Disease and Other Dementias", Harrison's Principles of Internal Medicine, Isselbacher et al., eds., McGraw–Hill, Inc., New York, pp. 2272–2273, 1991.

Brouillet et al., "Chronic Mitochondrial Energy Impairment Produces Selective Striatal Degeneration and . . . ", Proc. Natl. Acad. Sci. 92:7105–7109, 1995.

* cited by examiner

USE OF K-252A DERIVATIVE

This applications claims benefit of U.S. Provisional application Ser. No. 60/020,406, filed Jun. 25, 1996.

FIELD OF THE INVENTION

The invention relates to a ring-substituted derivative of K-252a for use in methods directed to ameliorating the deleterious effects of a variety of diseases, disorders and conditions.

BACKGROUND OF THE INVENTION

I. The Indolocarbazole K-252a

K-252a is a compound having an indolocarbazole skeleton [Japanese Published Unexamined Patent Application No. 41489/85 (U.S. Pat. No. 4,555,402)] with the stereochemistry shown in Formula I.

It has been reported that K-252a strongly inhibits protein kinase C (PKC) which plays a central role in regulating cell functions, and has various activities such as the action of inhibiting smooth muscle contraction (Jpn. J. Pharmacol. 43 (suppl.): 284, 1987), the action of inhibiting elongation of neurazone (J. Neuroscience, 8: 715, 1988), the action of inhibiting histamine release (Allergy, 43: 100, 1988), the action of inhibiting smooth muscle MLCK (J. Biol. Chem., 263: 6215, 1988), anti-inflammatory action (Acta Physiol. Hung., 80: 423, 1992), and the activity of cell survival (J. Neurochemistry, 64: 1502, 1995). It has also been disclosed in Experimental Cell Research, 193: 175–182, 1991, that K-252a has the activity of inhibiting IL-2 production.

In addition, it has been reported that derivatives of K-252a have PCK inhibitory activity, the activity of inhibiting histamine release (Japanese Published Unexamined Patent Application No. 295588/88), antitumor activity [Japanese Published Unexamined Patent Application No. 168689/89 (U.S. Pat. No. 4,877,776), WO 88/07045 (U.S. Pat. No. 4,923,986), WO 94/04541], the action of increasing blood platelets [WO 94/06799 (EP 630898A)], vasodepressor activity (Japanese Published Unexamined Patent Application No. 120388/87), the action of accelerating cholinergic neuron functions [WO 94/02488 (U.S. Pat. No. 5,461,146 and U.S. Pat. No. 5,621,100)] and, curative effect on prostate cancer [WO 94/27982 (U.S. Pat. No. 5,516,771)]. Selected amino-containing trindene compounds have been prepared by Beckmann rearrangement of the corresponding staurosporine oximes (WO 97/05140).

The indolocarbazoles are generally lypophilic. Because of this feature, the indolocarbazoles are able to cress biological membranes with relative ease, compared to proteins. Also indolocarbazoles generally have longer in vivo half lives than proteins.

In addition to K-252a itself, various derivatives of K-252a have been synthesized and tested for biological activity. Among the K-252a derivatives shown to have biological activity is a compound disclosed in Lewis et al., U.S. Pat. Nos. 5,461,146, and 5,621,100, and PCT Publication WO 94/02488, and designated therein as "Compound II-51." Compound II-51 has been shown to enhance the function of cholinergic neurons, striatal neurons, and sensory neurons.

II. Neurodegenerative Diseases and Disorders

Parkinson's disease is a neurodegenerative disorder that involves progressive and selective loss of dopaminergic neurons of the nigro-striatal pathway (Agid, Lancet: 337:1991). Administration of 1-methyl-4-phenyl-1,2,4,6-tetrahydropyridine (MPTP) to mice leads to dopaminergic neuron degeneration and serves as an animal model for the dopaminergic neuronal loss and behavioral deficits observed in Parkinson's disease. Peripheral administration of MPTP leads to a highly selective degeneration of the nigrostriatal dopaminergic neuronal system in humans, monkeys and mice (Heikkila et al., Science 224; 1451–1453, 1984; Burns et al., Proc Natl. Acad. Sci. USA 80:4546–4550, 1983).

Neurodegeneration in the MPTP mouse model has been well-characterized. Systemic administration of MPTP produces selective loss of dopamine content (and metabolites), tyrosine hydroxylase activity, and dopamine uptake sites in dopaminergic neurons of the murine striatum (Heikkila et al., Nature 311:467–469, 1984a,b; Tipton et al., J. Neurochem. 61:1191–1206, 1993). This effect is dose-dependent. Maximal loss occurs between 3 and 7 days post-lesion (Jackson-Lewis et al., Neurodegeneration 4:257–269, 1995). The dopaminergic cell bodies in the nigra are less sensitive to MPTP toxicity than their corresponding nerve terminals. At high MPTP doses, or multiple MPTP injections, substantial loss of TH immunopositive cells in the substantia nigra occurs within a week (Heikkila et al., Science 224; 1451–1453, 1984; Jackson-Lewis et al., Neurodegeneration 4:257–269, 1995). At lower MPTP doses, or with a single injection, loss of nigral tyrosine hydroxylase positive cells occurs later (Tatton et al., J. Neuroscience. Res. 30:666–672, 1991). Thus, at lower doses of MPTP and a short-time period after lesion, striatal damage can be observed in the absence of nigral tyrosine hydroxylase-positive cell loss. This neurodegenerative sequence is similar to that observed in the disease. The MPTP mouse model is a recognized and widely used model for the study of Parkinson's disease.

Non-cholinergic neurons that use γ-aminobutyric acid (GABA) as a neurotransmitter (i.e., GABA-ergic neurons) are widespread throughout the brain. For example, they are found in the nucleus basalis magnocellularis in the rodent (the equivalent region in the human brain is called nucleus basalis of Meynert), a region of the basal forebrain important in attention and memory functions. Damage to GABA-ergic neurons in the basal forebrain may also contribute to behavioral deficits in neurodegenerative diseases such as Alzheimer's disease (Dekker et al., Neurosci. and Biobehav. Rev., 15:299–317, 1991; Gallagher et al., Seminars in Neuroscience, 6;351–358, 1994; Torres et al., Neuroscience, 63:95–122, 1994).

Neurons in the basal forebrain die in several diseases of the central nervous system, notably Alzheimer's disease (Arendt et al., Acta Neuropathol. (Berl.) 61:101–108, 1983; Iraizoz et al., Neuroscience, 41:33–40, 1991; Vogels et al., Neurobiol. Aging, 11:3–13, 1990). A contributing factor in such neuronal cell death is glutamate excitotoxity, i.e. overstimulation of neurons by excess glutamate (Choi, Neuron, 1:623–634, 1988). Accordingly, several animal models of Alzheimer's disease use glutamate or a glutamate analog to produce excitotoxic death in the region of the basal forebrain where neuron death occurs, i.e., the nucleus basalis magnocellularis (Wenk, *Beh. Brain Res.,* 72:17–24, 1996).

Neuronal pathology in Alzheimer's disease is first seen in the entorhinal cortex, and loss of neurons in this region becomes severe as the disease progresses (Braak et al., *Acta Neuropathol.* 82:239–259, 1991; Hyman et al., *Ann. Neurol.* 20:472–481, 1986). Neurons in layer 2 of the entorhinal cortex project to the dentate syrus of the hippocampus, and this neuronal pathway plays an important role in memory formation (Levisohn et al., *Brain Res.* 564:230–244, 1991; Olton et al., *Brain Res.* 139:295–308, 1978; Steward et al., *Brain Res. Bull.* 2:41–48, 1977). Neurons in layer 2 of the entorhinal cortex, like many other neurons in the cerebral cortex, use glutamate as a neurotransmitter (Mattson et al., *Neuron* 1:865–876, 1988; White et al., *Nature* 270:356–357, 1977). Thus, loss of flutamatergic neurons in the entorhinal cortex contributes to the behavioural deficits seen in Alzheimer's disease and other neurological disorders.

III. Peripheral Neuropathy

Peripheral neuropathy generally refers to a disorder that affects the peripheral nerves, most often manifested as one or a combination of motor, sensory, sensorimotor, or autonomic neural dysfunction. The wide variety of morphologies exhibited by peripheral neuropathies can each be uniquely attributed to an equally wide variety of causes. For instance, peripheral neuropathies can be genetically acquired, can result from a systemic disease, or can be induced by a toxic agent. Some toxic agents that cause neurotoxicities are therapeutic drugs, antineoplastic agents, contaminants in foods or medicinals, and environmental and industrial pollutants.

In particular, chemotherapeutic agents known to cause sensory and/or motor neuropathies include vineristine, an antineoplastic drug used to treat haematological malignancies and sarcomas. The neurotoxicity is dose-related, and exhibits as reduced intestinal motility and peripheral neuropathy, expecially in the distal muscles of the hands and feet, postural hypotension, and atony of the urinary bladder. Similar problems have been documented with taxol and cisplatin (Mollman, 1990, *New Eng. Jour. Med.* 322:126–127), although cisplatin-related neurotoxicity can be alleviated with nerve growth factor (NGF) (Apfel, et al., 1992, *Annals of Neurology* 31:76–80). Although the neurotoxicity is sometimes reversible after removal of the neurotoxic agent, recovery can be a very slow process (Legha, 1986, *Medical Toxicology* 1:421–427; Olesen, et al., 1991, *Drug Safety* 6:302–314).

There are a number of inherited peripheral neuropathies, including: Rofsum's disease, A-betalipoproteinemia, Tangier disease, Krabbe's disease, Metachromatic leukodystrophy, Fabry's disease, Dejerine-Sottas syndrome, and others. Of all the inherited neuropathies, the most common by far is Charcot-Marie-Tooth disease (see also, U.S. Pat. No. 5,420,112 for additional information on peripheral neuropathies).

IV. Cytokines

Tumor necrosis factor α (TNF-α) and interleukin-1β (IL-1β) are polypeptides known to be involved in a number of inflammatory and metabolic processes in vivo. For a review which relates the role of TNF-α in inflammatory diseases, including septic shock, see *Ann. Rev. Immunol.* 7:625 (1980), and *Clinical Trials for the Treatment of Sepsis,* Sibbald, W. J. and Vincent, J.-L. (Eds.), Springer-Verlag Berlin Heidelberg 1995. It is generally accepted that the overproduction or inappropriate production of TNF-α is involved in several pathological conditions, including septic shock (Spooner et al., *Clinical Immunology and Immunopathology,* 62:p. S11 (1992)) and various other allergic and inflammatory conditions or diseases, including but not limited to rheumatoid arthritis, osteoarthritis, asthma, bronchitis, chronic obstructive airway disease, psoriasis, allergic rhinitis, dermatitis, and inflammatory bowel disease, and other autoimmune diseases. *Immunol. Res.* 10:122 (1991), *Science* 229:896 (1985) and *Proc. Natl. Acad. Sci.* 89:7375 (1992).

SUMMARY OF THE INVENTION

Generally, the invention features methodologies for ameliorating the deleterious effects of a variety of diseases, disorders and conditions by treating a subject in need thereof with a therapeutically effective amount of compound A.

More specifically, the invention features a method for treating the deleterious effects of diseases, disorders and conditions which lead to or cause the death of, or lead to or cause inhibition of the function of, certain neurons by enhancing the function or survival of a dopaminergic, GABA-ergic, or glutamatergic neuron in a mammal, comprising the step of contacting the neuron with Compound A. Typically, the mammal in which the neuron is found in a human. Typically, the dopaminergic, GABA-ergic, or glutamatergic neuron contacted with Compound A has impaired function, or is at risk of dying, because of a neurodegenerative disease. Typically, the neurodegenerative disease is Parkinson's disease or Alzheimer's disease.

More specifically, the invention also features a method of reducing a peripheral neuropathy comprising administering to a mammal a neuropathy-reducing amount of Compound A.

While it has been reported that the indolocarbazole compound K-252a reduces the lethality resulting from endotoxin administration, this ability has been ascribed to the ability of K-252a to inhibit protein kinases, especially protein kinase C (Inaba et al., *Jpn. J. Surg* 23:234 (1993). It has unexpectedly been found that Compound A, which has little or no inhibitory activity against PKC, provides surprisingly good activity as an inhibitor of TNF-α production and production of the cytokine IL-1β. Therefore, and with further specificity, the invention also features a method of inhibiting production of TNF-α and IL-1β in a mammal and a method of treating or alleviating inflammatory conditions or diseases, including but not limited to septic shock, rheumatoid arthritis, osteoarthritis, asthma, bronchitis, chronic obstructive airway disease, psoriasis, allergic rhinitis, dermatitis, and inflammatory bowel disease and other autoimmune diseases, which method comprises administering to said mammal an effective amount of Compound A and pharmaceutically acceptable salts thereof in combination with a pharmaceutically acceptable carrier.

As used herein, "Compound A" means the compound whose chemical structure is shown below.

Compound A is also referred to as Compound II-51 (Lewis et al., U.S. Pat. Nos. 5,461,146 and 5,621,100; WO 94/02488).

As used herein, "ameliorate" and "ameliorating" mean to therapeutically improve and/or therapeutically reduce and/or to make more therapeutically tolerable.

As used herein, "deleterious" means damaging and/or harmful and/or negative.

As used herein, the word "overproduction" when used to modify TNF-α and IL-1β means production of TNF-α and/or IL-1β leading to deleterious conditions such as, for example, septic shock, allergic conditions, inflammatory conditions, etc.

As used herein, the terms "inhibit" or "inhibiting" means that the presence of Compound A has a comparatively greater effect on reducing and/or prohibiting and/or preventing the production of a material contacted with Compound A than a comparative material not contacted with Compound A.

As used herein, the terms "enhance" or "enhancing" when used to modify the terms "function" or "survival" means that the presence of Compound A has a comparatively greater effect on the function and/or survival of the specified neuron that a comparative neuron not presented with Compound A. For example, and not by way of limitation, with respect to the survival of, e.g., a dopaminergic neuron, Compound A would evidence enhancement of the function of a dopaminergic neuronal population at risk of dying (due to, e.g., injury, a disease condition, a degenerative condition or natural progression) when compared to a dopaminergic neuronal population not presented with Compound A, if the treated population has a comparatively greater period of functionality than the non-treated population.

As used herein, "dopaminergic neuron" means a neuron that uses dopamine as a neurotransmitter.

As used herein, "GABA-ergic neuron" means a neuron that uses β-aminobutyric acid as a neurotransmitter.

As used herein, "glutamatergic neuron" means a neuron that uses glutamate as a neurotransmitter.

As used herein, "nbm" means nucleus basalis magnocellularis.

Unless otherwise defined, all technical and scientific terms used herein have the same meaning as commonly understood by one of ordinary skill in the art to which this invention pertains. Although methods and materials similar or equivalent to those described herein can be used in the practice or testing of the present invention, the preferred methods and materials are described below. All publications, patent applications, patents, and other references mentioned herein are incorporated by reference in their entirety. In case of conflict, the present document, including definitions, will control. Unless otherwise indicated, materials, methods, and examples described herein are illustrative only and not intended to be limiting. Various features and advantages of the invention will be apparent from the following detailed description and from the claims.

DETAILED DESCRIPTION

Generally, the invention features methodologies for ameliorating the deleterious effects of a variety of diseases, disorders and conditions by treating a subject in need thereof with a therapeutically effective amount of Compound A.

This invention provides a method for treating the deleterious effects of diseases, disorders and conditions which negatively affect the function and/or survival of neurons at risk of dying due to such diseases and disorders by enhancing the function or survival of specific types of neurons of the mammalian central nervous system. More particularly, the invention provides a method for enhancing the function or survival of dopaminergic neurons, GABA-ergic neurons, and glutamatergic neurons in a mammal by administering to the mammal Compound A, a ring-substituted K-252a derivative with the following chemical structure:

Compound A

Dopaminergic neurons, GABA-ergic neurons, and glutamatergic neurons are widespread in the mammalian central nervous system. Each of these three neuronal cell types suffers impaired function, or even death, in one or more neurodegenerative diseases of the central nervous system. Parkinson's disease involves progressive loss of dopaminergic neurons of the nigrostriatal pathway. Alzheimer's disease involves the death of various types of neurons, including GABA-ergic neurons in the nucleus basalis of Meynert of the basal forebrain. Alzheimer's disease also involves death of glutamatergic neurons in the entorhinal cortex.

One method of treating Parkinson's disease or Alzheimer's disease is to administer a compound that enhances the function or survival of dopaminergic neurons, GABA-ergic neurons, or glutamatergic neurons. Compound A is pharmacologically active in biological assays and in vivo models for enhanced function or survival of dopaminergic neurons, GABA-ergic neurons, and glutamatergic neurons. Therefore, the present invention has utility for treating Parkinson's disease or Alzheimer's disease. The invention, however, is not limited to the treatment of those diseases. The use of Compound A to enhance the function or survival of dopaminergic neurons, GABA-ergic neurons, or glutamatergic neurons whose impaired function or risk of dying results from causes other than Parkinson's disease or Alzheimer's disease is also within the scope of the present invention.

This invention also features a method of reducing a peripheral neuropath. The method involves administering a neuropathy-reducing amount of Compound A to a mammal. In various preferred embodiments, the mammal is a human, or an agricultureal or domestic mammal that develops a neuropathy, e.g., as a result of treatment of a neoplasm with a chemotherapeutic agent. Compound A can be administered in a manner deemed effective by one skilled in the art; a preferred mode of administration is subcutaneous injection.

As used herein, "peripheral neuropathy" refers to a disorder affecting a segment of the peripheral nervous system. The invention involves using Compound A to reduce a neurotoxicity, including, but not limited to, distal sensorimotor neuropathy, or autonomic neuropathies such as reduced motility of the gastrointestinal tract or atony of the urinary bladder.

Preferred neuropathies that can be effectively treated with Compound A include neuropathies associated with systemic disease, e.g., post-polio syndrome; genetically acquired neuropathies, e.g., Charcot-Marie-Tooth disease; and neuropathies caused by a toxic agent, e.g., acrylamide, or a chemotherapeutic agent, e.g., vincristine.

Where Compound A is used to treat a neuropathy induced by a toxic agent, it can be administered before, simultaneously with, or after exposure to the toxic agent, or before, during or after administration of a chemotherapeutic. Preferably, Compound A and the chemotherapeutic agent are each administered at effective time intervals, during an overlapping period of treatment. Compound A can be administered to the mammal following exposure to the neurotoxic agent, or following chemotherapy, to restore at least a portion of the neurofunction destroyed by the neurotoxic agent or chemotherapeutic. The chemotherapeutic can be any chemotherapeutic agent that causes neurotoxicity, such as vincristine, taxol, dideoxyinosine, or cisplatin.

By "toxic agent" or "neurotoxic agent," is meant a substance that through its chemical action injures, impairs, or inhibits the activity of a component of the nervous system. The list of neurotoxic agents that cause neuropathies is lengthy, and includes, but is not limited to, neoplastic agents such as vincristine, vinblastine, cisplatin, taxol, or dideoxy-compounds, e.g., dideoxyinosine; alcohol; metals; industrial toxins involved in occupational or environmental exposure; contaminants of food or medicinals; or over-doses of vitamins or therapeutic drugs, e.g., antibiotics such as penicillan or chloramphenicol, or megadoses of vitamins A, D, or B6. An extensive, although not complete, list of chemical compounds with neurotoxic side-effects is found in Table 1. Although this list provides examples of neurotoxic compounds, it is intended to exemplify, not limit, the scope of the invention. Other toxic agents can cause neuropathies, and can be characterized by methods known to one skilled in the art. By "exposure to a toxic agent" is meant that the toxic agent is made available to, or comes into contact with, a mammal of the invention. Exposure to a toxic agent can occur by direct administration, e.g., by ingestion or administration of a food, medicinal, or therapeutic agent, e.g., a chemotherapeutic agent, by accidental contamination, or by environmental exposure, e.g., aerial or aqueous exposure.

Despite the widely disparate morphologies and causes attributed to peripheral neuropathies in vivo, applicants have hypothesized that Compound A can be an effective means of preventing or treating such neuropathies in a mammal.

TABLE 1

AGENTS THAT CAUSE PERIPHERAL NEUROPATHY

| AGENT | ACTIVITY | AGENT | ACTIVITY |
| --- | --- | --- | --- |
| acetazolamide | diuretic | imipramine | antidepressant |
| acrylamide | flocculent, grouting agent | indomethacin | anti-inflammatory |
| adriamycin | antineoplastic | inorganic lead | toxic metal in paint, etc. |
| alcohol (ethanol) | solvent, recreational drug | isoniazid | antituberculous |
| almitrine | respiratory stimulant | lithium | antidepressant |
| amiodarone | antiarrhythmic | methylmercury | industrial waste |
| amphotericin | antimicrobial | metformin | antidiabetic |
| arsenic | herbicide, insecticide | methyldrazine | synthetic intermediate |
| aurothioglucose | antirheumatic | metronidazole | antiprotozoal |
| barbiturates | anticorvulsant, sedative | misonidazole | radiosensitizer |
| buckthorn | toxic berry | nitrofurantoin | urinary antiseptic |
| carbamates | insecticide | nitrogen mustard | antineoplastic, nerve gas |
| carbon disulfide ($CS_2$) | industrial | nitrous oxide | anesthetic |
| chloramphenicol | antibacterial | organophosphates | insecticides |

TABLE 1-continued

AGENTS THAT CAUSE PERIPHERAL NEUROPATHY

| AGENT | ACTIVITY | AGENT | ACTIVITY |
|---|---|---|---|
| chloroquine | antimalarial | ospolot | anticonvulsant |
| cholestyramine | antihyperlipoproteinemic | penicillin | antibacterial |
| cisplatin | antineoplastic | perhexiline | antiarrhythmic |
| clioquinol | amebicide, antibacterial | perhexiline maleate | antiarrhythmic |
| colestipol | antihyperlipoproteinemic | phenytoin | anticonvulsant |
| colchicine | gout suppressant | platinum | drug component |
| colistin | antimicrobial | primidone | anticonvulsant |
| cycloserine | antibacterial | procarbazine | antineoplastic |
| cytarabine | antineoplastic | pyridoxine | vitamin B6 |
| dapsone | dermatologic including leprosy | sodium cyanate | anti-sickling |
| dideoxycytidine | antineoplastic | streptomycin | antimicrobial |
| dideoxyInosine | antineoplastic | sulphonamides | antimicrobial |
| dideoxythymidine | antiviral | suramin | antineoplastic |
| disulfiram | antialcohol | tamoxifen | antineoplastic |
| doxorubicin | antineoplastic | taxol | antineoplastic |
| ethambutol | antibacterial | thalidomide | antileprous |
| ethionamide | antibacterial | thallium | rat poison |
| glutethtmide | sedative, hypnotic | triamterene | diuretic |
| gold | antirheumatic | trimethyltin | toxic metal |
| hexacarbons | solvents | L-tryptophan | health food additive |
| hormonal contraceptives | | vincristine | antineoplastic |
| hexamethylolmelamine | fireproofing, creaseproofing | vinblastine | antineoplastic |
| hydralazine | antihypertensive | vindesine | antineoplastic |
| hydroxychloroquine | antirheumatic | vitamin A | mega doses |
| | | vitamin D | mega doses |

Compound A has also been demonstrated to inhibit production of the cytokine TNF-α, despite having little or no inhibitory activity against PKC. Compound A also inhibits the production of the cytokine IL-1β. The production of TNF-α is associated with a variety of diseases and disorders such that the inhibition thereof via use of Compound A can beneficially provide value to a subject in need of such inhibition of TNF-α production.

Accordingly, Compound A can also be utilized to inhibit production of TNF-α in a mammal and/or a method of treating or alleviating inflammatory conditions or disease, including but not limited to septic shock, rheumatoid arthritis, osteoarthritis, asthma, bronchitis, chronic obstructive airway disease, psoriasis, allergic rhinitis, dermatitis, and inflammatory bowel disease, and other autoimmune diseases which method comprises administering to said mammal a therapeutically effective amount of Compound A.

For use in the present invention, Compound A can be formulated into a pharmaceutical composition by admixture with pharmaceutically acceptable nontoxic excipients and carriers. Such a composition can be prepared for administration by any of various routes. Routes of administration and preferred dosage forms include the following: parenteral, preferably in the form of liquid solutions of suspensions; oral, preferably in the form of tablets of capsules; intranasal, preferably particularly in the form of powders, nasal drops, or aerosols; and dermal, via, for example, trans-dermal patches.

Composition A can be conveniently administered in unit dosage form and may be prepared by any of the methods well known in the pharmaceutical art, for example, as described in *Remington's Pharmaceutical Sciences* (Mack Pub. Co., Easton, Pa., 1980). Formulations for parenteral administration may contain as common excipients sterile water or saline, polyalkylene glycols such as polyethylene glycol, oils and vegetable origin, hydrogenated naphthalenes and the like. In particular, biocompatible, biodegradable lactide polymer, lactide/glycolide copolymer, or polyoxyethylene-polyoxypropylene copolymers may be useful excipients to control the release of the active compounds. Other potentially useful parenteral delivery systems for Compound A include ethylene-vinyl acetate copolymer particles, osmotic pumps, implantable infusion systems, and liposomes, Formulations for inhalation administration contain as excipients, for example, lactose, or may be aqueous solutions containing, for example, lactose, or may be aqueous solutions containing, for example, polyoxyethylene-9-lauryl ether, glycocholate and deoxycholate, or oily solutions for administration in the form of nasal drops, or as a gel to be applied intranasally. Formulations for parenteral administration may also include glycocholate for buccal administration, a salicylate for rectal administration, or citric acid for vaginal administration. Formulations for transdermal patches are preferably lipophilic emulsions.

Compound A can be employed as the sole active ingredient in a pharmaceutical composition. Alternatively, it can be used in combination with other active ingredients, e.g., growth factors that facilitate neuronal survival or axonal regeneration in diseases or disorders.

The concentration of Compound A used in the practice of this invention in a therapeutic composition can vary. The concentration will depend upon factors such as the total dosage of the drug to be administered and the route of administration. Compound A typically would be provided in an aqueots physiological buffer solution containing about 0.1 to 10% w/v for parenteral administration. Typical dose ranges are from about 1 μg/kg to about 1 g/kg of body weight per day; a preferred dose range is from about 0.01 mg/kg to 100 mg/kg of body weight per day. A preferred dosage of Compound A to be administered is likely to depend on variables such as the type and extent of progression of the disease or disorder, the overall health status of the particular patient, the relative efficacy of Compound A for the particular disease or disorder treated, the particular formulation used, and its route of administration.

Compound A for use in the present invention is preferably obtained according to the methods described in Lewis et al., U.S. Pat. No. 5,461,146.

The present invention will be further illustrated by the following examples. These examples are not to be construed as limiting the scope of the invention, nor the scope of the claims appended hereto.

EXAMPLES

Example 1

Pharmacological Activity on Dopaminergic Neurons

Experiments were conducted using Compound A in MPTP-lesioned dopaminergic neurons in mice (MPTP mouse model). A single s.c. dose of MPTP (20 mg/kg) provided to C57 black mice produced approximately 60% loss of striatal tyrosine hydroxylase activity. Administration of Compound A, at daily doses ranging from 0.01 to 10 mg/kg (s.c.), to such MPTP-treated mice reduced the loss of striatal tyrosine hydroxylase activity. These data are shown in Table 2.

TABLE 2

Striatal Tyrosine Hydroxylase (TH) Activity in Low-Dose MPTP-Treated Mice[a]

| Treatment | Striatal TH Activity (± SEM) | % of Unlesioned Control |
|---|---|---|
| Unlesioned | 19.06 ± 1.06 | 100 ± 5.6 |
| MPTP-Lesioned | 7.40 ± 1.07 | 39 ± 5.6 |
| MPTP Lesioned (Vehicle) | 6.99 ± 0.75 | 37 ± 4.0 |
| MPTP Lesioned + Cmpd A | | |
| (0.01 mg/kg) | 7.76 ± 1.23 | 41 ± 5.3 |
| (0.03 mg/kg) | 10.48 ± 0.92* | 55 ± 3.9 |
| (0.10 mg/kg) | 11.51 ± 0.80* | 60 ± 6.5* |
| (0.30 mg/kg) | 11.89 ± 1.34* | 62 ± 5.0* |
| (1.0 mg/kg) | 10.39 ± 1.39* | 54 ± 7.0* |
| (3.0 mg/kg) | 9.66 ± 1.10 | 51 ± 5.8 |
| (10.0 mg/kg) | 9.77 ± 0.70 | 51 ± 3.7 |

[a]Average of three dose - response experiments.

Mice were treated with MPTP (20 mg/kg; s.c.) 4–6 hours after the first Compound A injection. Compound A was then injected every day until the end of the experiment, which was 7 days in duration. Striata were assessed for tyrosine hydroxylase enzyme activity. Asterisk indicates statistically significant difference (p<0.05) from MPTP-Vehicle treated animals.

In a separate experiment, the activities of Compound A were assessed in a high dose MPTP-mouse model. A single 40 mg/kg injection of MPTP produced a 95% depletion in striatal tyrosine hydroxylase enzyme activity 7 days post-injection. Administration of Compound A at daily doses of between 0.03 and 3.0 mg/kg reduced the magnitude of the lesion, in a dose dependent manner. These data are shown in Table 3.

TABLE 3

Striatal Tyrosine Hydroxylase (TH) Activity in High-Dose MPTP-Treated Mice[a]

| Treatment | Striatal TH Activity (± SEM) | % Unlesioned Control |
|---|---|---|
| Unlesioned | 23.1 ± 1.6 | 100 ± 7.0 |
| MPTP-Lesioned (Vehicle) | 1.6 ± 0.6 | 7 ± 3.0 |
| MPTP-Lesioned + Cmpd A | | |
| (0.03 mg/kg) | 1.8 ± 0.6 | 8 ± 2.5 |
| (0.3 mg/kg) | 2.7 ± 0.6 | 12 ± 2.5 |
| (3.0 mg/kg) | 5.3 ± 1.8* | 23 ± 8.0* |

[a]Data are from a single experiment.

Mice were treated with MPTP (40 mg/kg; s.c.) 4–6 hrs after the first Compound A injection. Compound A was then injected every day until the end of the experiment which was 7 days in duration. Striata were assessed for tyrosine hydroxylase enzyme activity. Asterisk indicates statistically significant difference (p<0.05) from MPTP-Vehicle treated animals.

Figure 1:
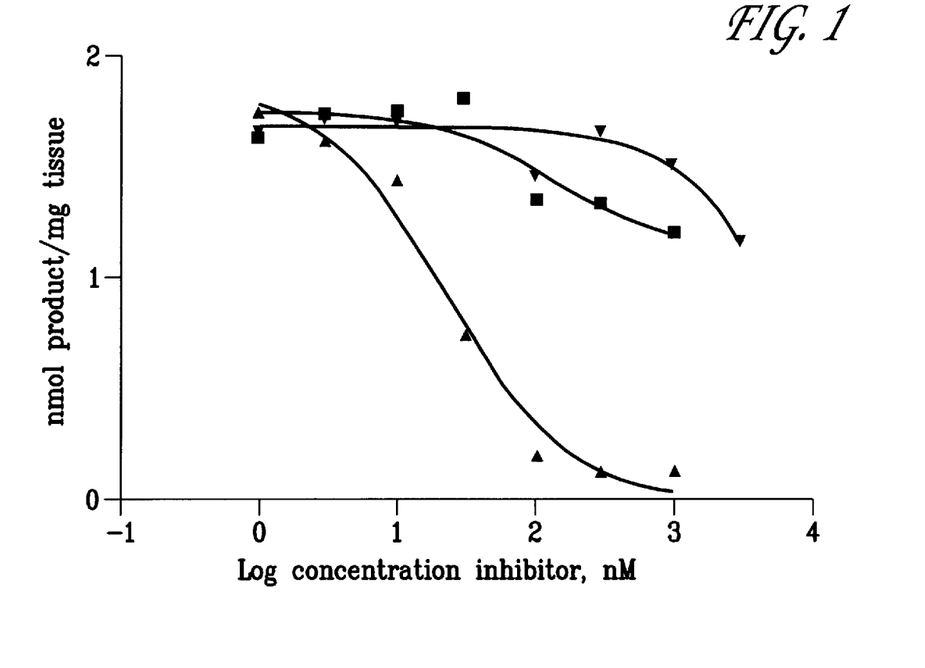
FIG. 1 is a graph of data demonstrating that Compound A is not a monoamine oxidase-A inhibitor. The $IC_{50}$ of Clorgyline was 21 nm. Upright triangles, Clorgyline; inverted triangles, Compound A; squares, L-deprenyl.
Figure 2:
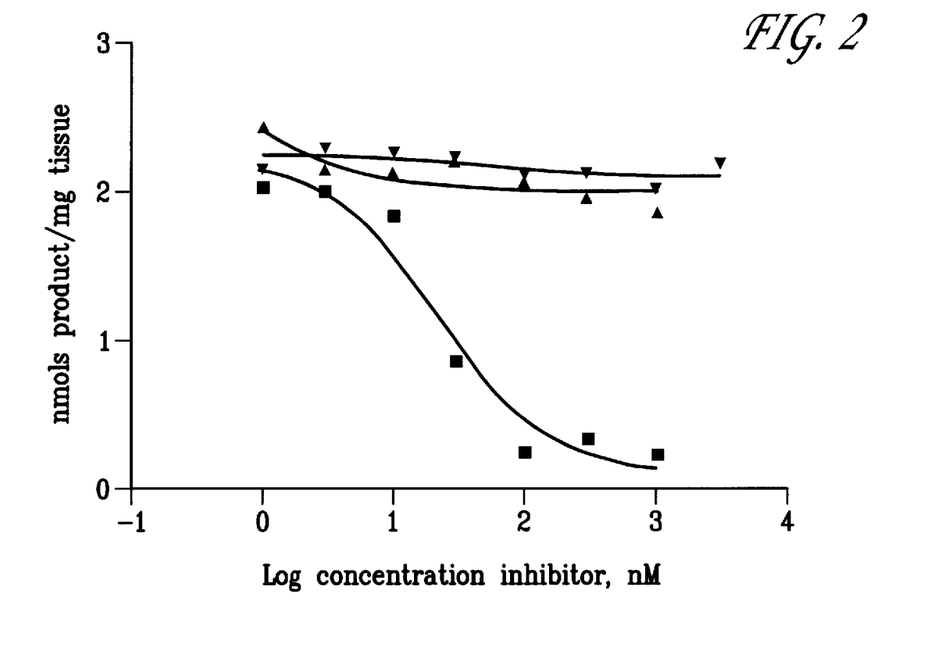
FIG. 2 is a graph of data demonstrating that Compound A is not a monoamine oxidase-B inhibitor. The $IC_{50}$ of Clorgyline was 21 nm. Upright triangles, Clorgyline; inverted triangles, Compound A; squares, L-deprenyl.

MPTP-mediated dopaminergic toxicity is dependent on MAO mediated conversion of MPTP to MPP$^+$ (1-methyl-4-phenylpyridinium ion) and uptake of MPP$^+$ into dopaminergic neurons. Compounds found to be active in the MPTP-mouse model should be determined not to be inhibitors of MAO or dopamine uptake. Compound A has been found not to inhibit monoamine oxidase A or B in vitro (FIGS. 1 and 2) or block uptake of catecholamines into nerve endings, indicating that this compound does not prevent the metabolic conversion of MPTP to MPP$^+$ or inhibit the active uptake of MPP$^+$ into dopaminergic neurons.

These data demonstrating efficacy of Compound A in the MPTP-mouse dopaminergic lesion model indicate utility of Compound A in the treatment of neurodegenerative disorders such as Parkinson's disease.

Example 2

Pharmacological Activity on GABA-ergic Neurons

Compound A was tested for its ability to prevent depletion (e.g., enhance the survival) of GABA-ergic neurons in the nucleus basalis magnocellularis, using the well-established ibotenic acid lesion mode. Ibotenic acid, an excitotoxin, is known to reduce numbers of GABA-expressing neurons in the nbm region (Lindefors et al., *Neurosci. Lett.*, 135:262–264, 1992; Shaugnessy et al., *Brain Res.*, 637:15–26, 1994).

Adult male Sprague-Dawley rats received injections of ibotenic acid (5.0 g) into the nbm unilaterally. The rats were then dosed with Compound A (0.03 mg/kg) via subcutaneous injection beginning 18 hours after the lesion, and continuing q.o.d. until 18 days post-lesion. Tissue sections were then collected throughout the rostral-caudal extent of the nbm, and processed to detect glutamic acid decarboxylase, an enzyme required for biosynthesis of GABA. The numbers of neurons expressing glutamic acid decarboxylase were then counted throughout the rostral-caudal extent of the nucleus basalis magnocellularis, in a region where glutamic acid decarboxylase-expressing neurons of the nbm are easily distinguished from glutamic acid decarboxylase-expressing neurons in adjacent structures (white matter medial and ventral to the globus pallidus). The results were expressed as percent glutamic acid decarboxylase-expressing neurons on the lesioned side relative to the number on the opposite, unlesioned side. The results were also calculated separately for the rostral nbm, mid-nmb, and caudal nbm.

A mean of 78 (±16 s.c.m.) percent glutamic acid decarboxylase neurons were counted in the rostral nbm of animals receiving Compound A, compared to 34 (±19 s.e.m.) percent in animals receiving vehicle only, a statistically significant difference by t test ($p<0.05$). No statistically significant differences between Compound A-treated animals and vehicle-only (control) animals were seen in mid-nbm or caudal nbm.

These results demonstrate that Compound A can protect against a GABA-ergic neuron loss that results from an excitotoxic lesion, and thus has a neurotrophic effect on that neuronal population.

Example 3

Pharmacological Activity on nbm Neurons

To test directly the ability of Compound A to prevent excitotoxic neuron death, nbm neurons in adult male Sprague-Dawley rats were first labeled with a long-lasting marker. This was done by injecting Fluoro-Gold (FG), a neuronal tracer that is taken up by nerve terminals and transported back to the cell body (Book et al., *J. Neuropath. Exp. Neurology*, 53:95–102, 1994), into target regions of nbm neurons in the frontal and parietal cortex. 7–10 days later the animals received lesion of the nbm unilaterally, using 5 μg of ibotenic acid. Beginning 18 hours after this lesion, the animals received Compound A (0.03 mg/kg) via subcutaneous injection, every other day until 18 days post-lesion. Tissue sections were collected throughout the entire rostral-caudal extent of the nbm on both sides of the brain, and numbers of nbm neurons with the FG label were counted. The counts were corrected for size differences using standard procedures, and the results expressed as the percent of labeled neurons in the nbm on the lesioned side of each animal relative to the number of labeled neurons in the nbm on the opposite unlesioned side of the brain.

Figure 3:
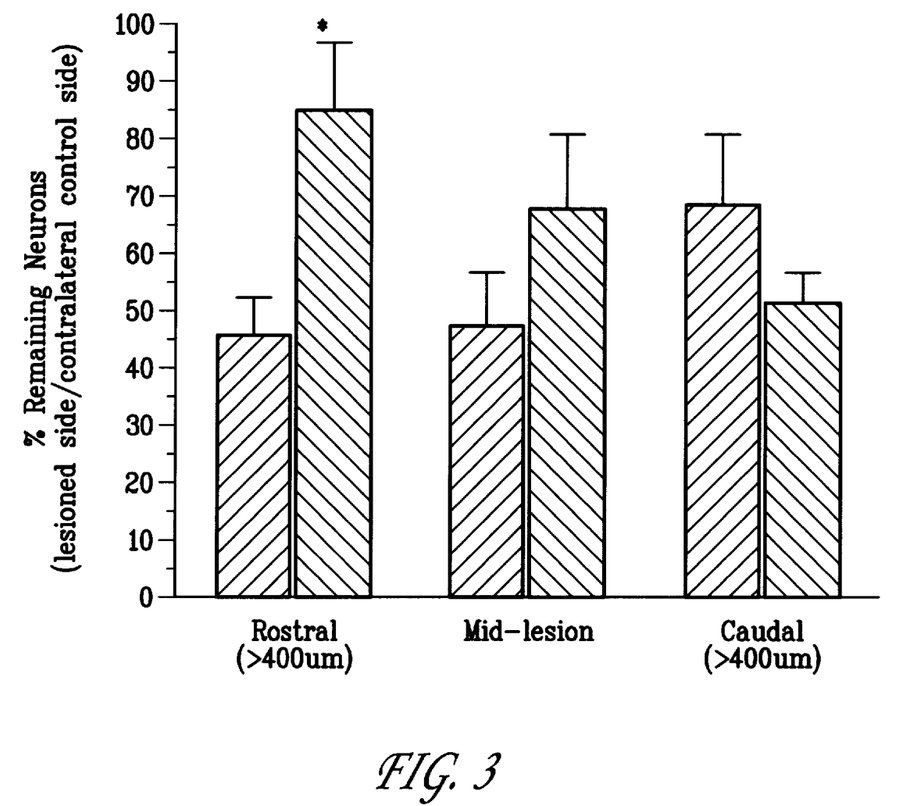
FIG. 3 is a bar graph showing that animals receiving Compound A (light bars) had significantly more Fluoro-Gold-labeled neurons in the rostral portion of the lesioned nbm (over 400 μm from the midpoint of the lesion), compared to lesioned animals receiving vehicle only (dark bars). *=P<0.05 by Newman-Keuls test.

Animals receiving compound A had significantly more FG-labeled neurons in the rostral portion of the lesioned nbm (over 400 μm from the mid-point of the lesion), compared to lesioned animals receiving vehicle only (FIG. 3). At mid-lesion and caudal to the lesion Compound A had a declining effect.

These results demonstrate directly that Compound A can prevent the loss of pre-labeled neurons in the nbm that results from excitotoxic damage.

Example 4

Long-Lasting Functional Improvement Upon Short Term Dosing with Compound A

Figure 4:
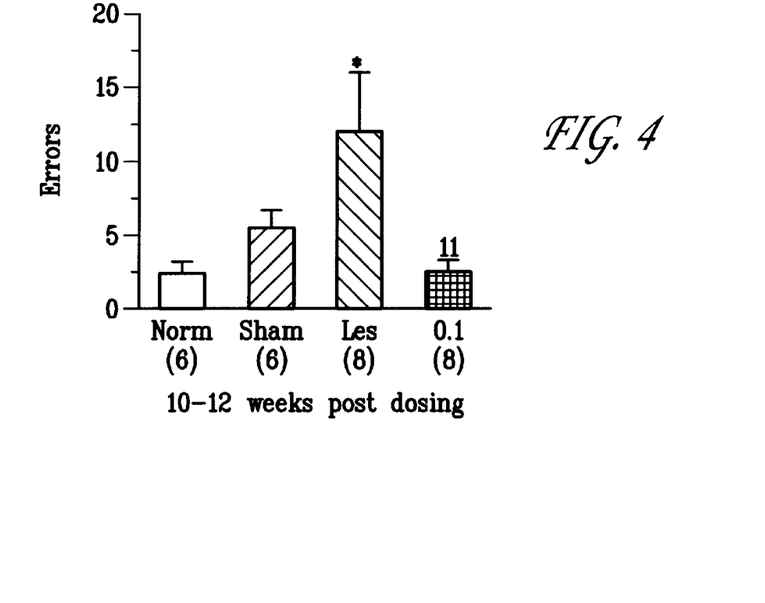
FIG. 4 is a bar graph showing the total number of errors committed in the T-maze rewarded alternation task by normal control animals, sham surgery animals, surgically-lesioned animals receiving vehicle only ("Les") and surgically-lesioned animals receiving Compound A at a dose of 0.1 mg/kg q.o.d. ("0.1"). Numbers of animals in each group are shown in parentheses. *=P<0.05 compared to Sham, ¶¶=P<0.01 compared to Les, by Newman-Keuls tests.

Adult male Sprague-Dawley rats were first trained to alternate responses in a standard rewarded-alternation T-maze task (Hepler et al., *J. Neurosci.*, 5:866–873, 1985). The animals then received bilateral lesions of the nucleus basalis magnocellularis, to impair performance in T-maze tasks (e.g., Salamone et al., *Behav. Brain Res.*, 13:63–70, 1984). Beginning 18 hours after the lesion, the animals received Compound A via subcutaneous injection (0.1 mg/kg) every other day until 12 days post-lesion. Twenty-four hours following the last injection all animals were placed in the T-maze once a day, until their alternation performance reached pre-operative levels, which took anywhere from 3 to 10 days. After reaching criterion, the animals were not further tested for 8–10 weeks. At that point the animals were again placed in the T-maze, once a day until they reached pre-operative performance. The total number of errors the animals committed during this test is shown in FIG. 4. The lesioned animals receiving vehicle only committed significantly more errors than either unoperated normals or sham-operates, while lesioned animals that received Compound A 10–12 weeks previously were not different from normals.

These results demonstrate that Compound A produces a chronic improvement in a behavior reflective of an improvement in attention or memory several months after dosing has ceased.

Example 5

Efficiency of Compound A in Entorhinal Cortex Lesion Model

Glutamate-containing neurons in layer 2 of the entorhinal cortex project to the molecular layer of the dentate gyrus, where they form synapses on the dendrites of the dentate gyrus granule cells. A lesion can be created in layer 2 of entorhinal cortex by stereotaxic injection of the excitotoxin N-methyl-D-asparate (NMDA). Under sodium pentobarbitol anesthesia, rats received an injection of NMDA (15 nmols/site) at each of 2 sites in the entorhinal cortex. Two weeks later, the rats were sacrificed and perfused with a 50 mM sodium sulfide solution. The brains were removed, sectioned in the horizontal plane at a thickness of 40 μm, and stained with either Cresyl violet or Timm'stain. The survival of neurons in layer 2 of entorhinal cortex was assessed in Cresyl violet stained sections, while the integrity of their axon terminals in the molecular layer of the dentate gyrus was measured in alternate sections stained with Timm's stain.

Injection of NMDA destroyed 62±11% (s.e.m.) of entorhinal layer 2 and decreased the area of the dentate gyrus middle molecular layer by 19±6% (s.e.m.). Daily treatment with Compound A (1 mg/kg, s.c.), with the first injection given immediately after injection of NMDA, reduced the loss of entorhinal layer 2 neurons to 22±10% (s.e.m.) ($p<0.05$, 't' test) and prevented the decrease in area of the middle molecular layer ($p<0.05$, 't' test). Thus, Compound A protected neurons in the entorhinal cortex from an excitotoxic lesion and maintained the integrity of their axon terminals in the dentate gyrus.

These data demonstrate the efficacy of Compound A in protecting glutamatergic neurons of the entorhinal cortex. Lesions of entorhinal cortex in animal models have been shown to produce memory deficits, and severe degeneration of these neurons occurs in Alzheimer's disease. This supports the position that Compound A is useful in treating neurological disorders that involve loss of or damage to glutamatergic neurons and neurons of the cerebral cortex, including but not limited to Alzheimer's disease, stroke and head trauma.

Example 6

Effect of Compound A on Acrylamide-Induced peripheral Neuropathy

Acrylamide produces a "dying back" central-peripheral distal neuropathy in humans and animals. The lesion is a mixed sensory/motor neuropathy characterized by weakness, tremor and ataxia in humans. In animals, acrylamide produces changes in behavior (sensory, motor and proprioceptive), histopathology, electrophysiology and weight loss. In the periphery, large diameter, long axon, Ab fibers are preferentially affected by acrylamide. In rats, acrylamide administration produces an axonopathy as measured by increased landing foot spread (LFS), a measure of proprioception.

Acrylamide-induced neuropathy is a model of chemically induced toxicity. It differs from other chemically-induced models (such as chemotherapeutic models) in that the duration is relatively short (3 weeks) and the animals are in relatively good health. Acrylamide does not produce gross systemic toxicity.

Male Sprague-Dawley rats weighing 250 grams at the start of the experiment were used. Acrylamide (50 mg/kg, IP) was administered three times/week for three weeks. The animals were dropped from a height of 30 cm and the distance between the hindfeet was recorded (Edwards, P. M. and Parker, V. H. (1977) "A simple, sensitive, and objective method for early assessment of acrylamide neuropathy in rats." *Toxicol. Appl Pharmacol,* 40:589–591). Compound A (0.1, 0.3 or 1.0 mg/kg, s.c. in 5% solutol) was administered once daily for the duration of the experiment.

Figure 5:
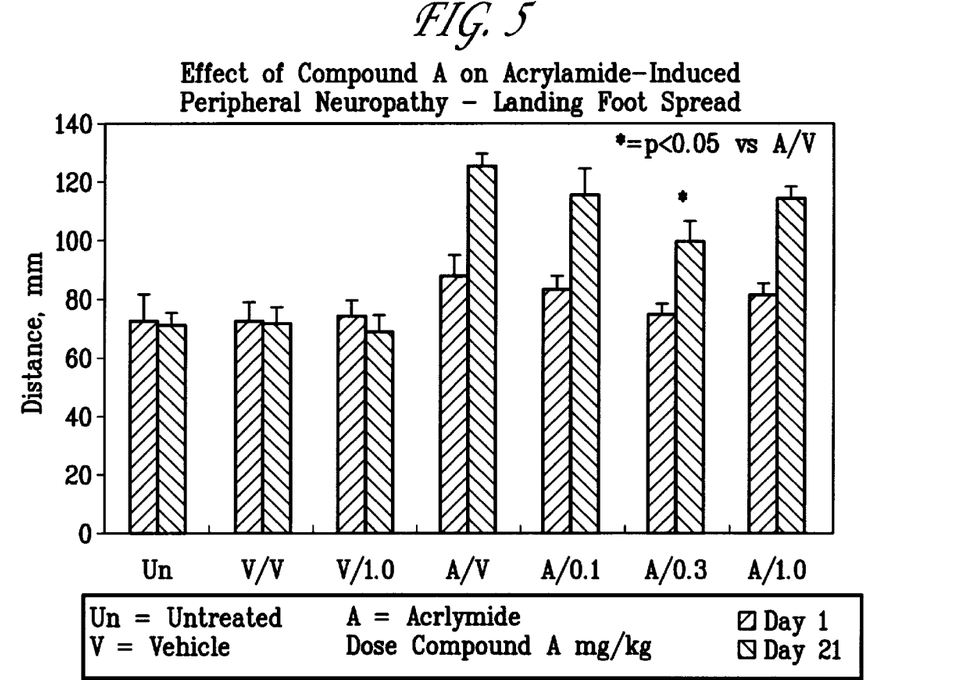
FIG. 5 shows the effect of Compound A on acrylamide-induced peripheral neuropathy.

Acrylamide-treated animals had larger distances in the LFS than the vehicle treated animals. Compound A (0.3 mg/kg/day) reduced the magnitude of the increase in LFS produced by acrylamide (FIG. 5).

These data indicate that Compound A is useful for the treatment of peripheral neuropathies.

Example 7

Failure of Compound A to Inhibit Protein Kinase C, In Vitro

The protein kinase C assay and the inhibition of protein kinase C by K-252a is disclosed in U.S. Pat. No. 4,923,986 and Kase, H. et.al., (eds.) Japan Scientific Societies Press, Tokyo, pp 293–296, (1988). By means of an essentially similar assay, it was found that K-252a inhibits protein kinase C with an $IC_{50}$ of 0.028 $\mu$M while the $IC_{50}$ of Compound A is 16.0 $\mu$M, i.e., 570 fold less active. Compound A has an $IC_{50}$ of 139 nM, as an inhibitor of the production of TNF-α, and an $IC_{50}$ value of 261 nM as an inhibitor of the production of IL-1β, concentrations at which Compound A is inactive as an inhibitor of protein kinase C.

Example 8

In Vitro Inhibition of TNF-α and IL-1β Production by Compound A

The ability of Compound A to inhibit the induction of TNF-α was demonstrated by use of a standard in vitro pharmacological testing procedure as described below. Stock solutions consisting of 4 mM Compound A, in 100% DMSO, were stored at 4° C. Cell culture medium RPMI 1640 (Media Tech, Herndon, Va.) and fetal bovine serum (Hyclone, Logan, Utah) comprised the test medium. Lipopolysaccharide (LPS) (Sigma, St. Louis, Mo.) from *E. coli* serotype 0.111:B4, extracted with trichloroacetic acid, was used. Stock solutions of LPS were prepared and stored at 4° C. in phosphate-buffered saline (PBS). ELISA kits for assaying tumor necrosis factor alpha (TNF-α) and IL-1β were purchased from Boehringer-Mannheim, (Indianapolis, Ind.) and were used according to the manufacturer's instructions. THP-1 cells, a human monocyte-derived cell line, was obtained from the American Type Culture Collection (ATCC TIB 202). Cells were grown in RPMI 1640 containing 10% fetal bovine serum (medium) in a humidified atmosphere of 5% $CO_2$:95% air at 37° C. Experiments were performed in 24 well culture plates (Nunc) with $5 \times 10^5$ THP-1 cells in 1 ml of medium. Cells were incubated with LPS at 2 ug/ml to induce TNF-α. After a 3-hr incubation period, the cells and medium were centrifuged at 1,000×g for 5 min, and the resulting supernatant fluid was either assayed immediately for TNF-α or stored at −70° C. and assayed later. Media samples were measured for content of TNF-α and IL-1β by Elisa assays.

To test Compound A for the ability to inhibit the induction of TNF-α, cells were incubated with varying concentrations of Compound A for 1 hr prior to the addition of LPS. Compounds were diluted so that DMSO was never present in the cell culture medium at a concentration higher than 0.1%. Compound A was tested and assayed as described above for its ability to inhibit TNF-α and IL-1β production.

Example 9

Inhibition of LPS-Induced TNF-α and IL-1β in the Serum of Mice.

Sixty female C57BL mice (4–6 weeks old) were divided into six groups, each with 10 animals. Three groups (1,3,5) received vehicle only (PBS containing 0.1% TEA (tetraethyl ammonium hydrochloride)), 200 $\mu$l/mouse via intraperitoneal (ip) administration. The other three groups (2,4,6) received Compound A (30 mg/kg in 200 $\mu$l, ip) of vehicle (PBS containing 10% of the ethyl ester of 12-hydroxystearic acid; solutol). Two hours later, the animals received by ip administration, 0.1 mg/kg of LPS (groups 1 & 2), 0.5 mg/kg of LPS (groups 3 & 4), and 1.0 mg/kg of LPS (groups 5 % 6). Two hours after LPS administration, all of the animals were sacrificed, and plasma samples were obtained and assayed for their TNF-60 and IL-1β content. Assays were carried out as described in Example 8.

Data are summarized in Table 4. The numbers in () are the group numbers as described above. N indicates the number of animals from which plasma measurements where made. ND=not done.

TABLE 4

| LPS dose | TNF-α (pg/ml) | | IL-1β (pg/ml) | |
|---|---|---|---|---|
| mg/mouse, ip | Vehicle | CMP A | Vehicle | Cmp A |
| 0.1 | (1)<br>6129 ± 676<br>N = 10 | (2)<br>2714 ± 449*<br>N = 10 | ND | ND |
| 0.5 | (3)<br>7141 ± 1113<br>N = 9 | (4)<br>3766 ± 375*<br>N = 7 | ND | ND |
| 1.0 | (5)<br>3745 ± 610<br>N = 8 | (6)<br>2399 ± 1399<br>N = 9 | (5)<br>300 ± 87<br>N = 8 | (6)<br>59 ± 19*<br>N = 8 |

*Indicates statistical difference from vehicle-treated control (p < 0.05).

As shown in Table 4, LPS administration to the mice caused the production by those mice of TNF-α, and the amount of TNF-α produced was markedly inhibited by a two hour pretreatment with Compound A. Pretreatment with Compound A also markedly inhibited the production of IL-1β, produced in response to the administration of 1.0 mg/kg of LPS.

Example 10

Prevention of LPS-Induced Death in Mice

Forty mice were divided into three groups, two groups consisting of ten mice and one group of twenty mice. Administrations of vehicles, LPS, and Compound A were intraperitoneal. Group 1 (n=10) mice received vehicle (phosphate buffered saline for LPS, 200 $\mu$l/mouse) at time zero and vehicle for Compound A (200 $\mu$l/mouse) 2 hours later. Group 2 (n=10) mice received the vehicle for Compound A at zero time (200 $\mu$l/mouse) and LPS (2 mg in 200 $\mu$l/mouse) for two hours later. Group 3 (n=20) received Compound A (30 mg/kg in 200 $\mu$l of vehicle) at time zero and LPS (2 mg in 200 $\mu$l/mouse) two hours later.

The administration of LPS caused 90% mortality within 20 hours and 100% mortality by 42 hours after administra- tion. In the group of animals which received Compound A two hours prior to receiving LPS, there was 25% mortality at 20 hours after LPS administration, 75% mortality at 42 hours after LPS, and 80% mortality one week after LPS administration. Vehicle treatments were well tolerated and caused no deaths.

Those skilled in the art will appreciate that numerous changes and modifications may be made to the preferred embodiments of the invention and that such changes and modifications may be made without departing from the spirit of the invention. It is therefore intended that the appended claims cover all equivalent variations as fall within the true spirit and scope of the invention. Documents cited throughout this patent disclosure are hereby incorporated herein by reference.

What is claimed is:

1. A method for treating an inflammatory condition or disease comprising administering to a host in need of such treatment a therapeutically effective amount of a compound represented by the formula 2. The method of claim 1, wherein the inflammatory condition or disease is selected from the group consisting of septic shock, rheumatoid arthritis, osteroarthritis, asthma, bronchitis, chronic obstructive airway disease, psoriasis, alergic rhinitis, dermatitis, and inflammatory bowel disease.

* * * * *

UNITED STATES PATENT AND TRADEMARK OFFICE
CERTIFICATE OF CORRECTION

PATENT NO. : 6,184,217 B1
DATED : February 6, 2001
INVENTOR(S) : Engber et al.

It is certified that error appears in the above-identified patent and that said Letters Patent is hereby corrected as shown below:

Title page,
Item [56], References Cited, FOREIGN PATENT DOCUMENTS, at "36-295589", please delete "36-295589" and insert -- 63-295589 -- therefor.
OTHER PUBLICATIONS, "Dunnett, S. et al." reference, please delete "totixic" and insert -- toxic -- therefor;
"McManamann, J. et al." reference, please delete "Notoneurons" and insert -- Motoneurons -- therefor; and
"Olton, D. et al." reference, please delete "*Progerss*" and insert -- *Progress* -- therefor.

Column 3,
Line 11, please delete "syrus" and insert -- gyrus -- therefor.
Line 19, please delete "flutamatergic" and insert -- glutamatergic -- therefor.
Line 20, please delete "behavioural" and insert -- behavioral -- therefor.
Line 40, please delete "expecially" and insert -- especially -- therefor.

Column 8,
Table I, third column, please delete "methyldrazine" and insert -- methylhydrazine -- therefor.
Table I, second column, please delete "anticorvulsant" and insert -- anticonvulsant -- therefor.

Column 9,
Table I, first column, please delete "dideoxylnosine" and insert -- dideoxyinosine -- therefor.
Table I, first column, please delete "glutethtmide" and insert -- glutethimide -- therefor.

Column 13,
Line 27, please delete "lesion" and insert -- lesions -- therefor.

Column 14,
Line 26, please delete "Timm'" and insert -- Timm's -- therefor.

UNITED STATES PATENT AND TRADEMARK OFFICE
CERTIFICATE OF CORRECTION

PATENT NO. : 6,184,217 B1
DATED : February 6, 2001
INVENTOR(S) : Engber et al.

It is certified that error appears in the above-identified patent and that said Letters Patent is hereby corrected as shown below:

Column 16,
Line 28, please delete "where" and insert -- were -- therefor.

Signed and Sealed this

Twenty-second Day of June, 2004

JON W. DUDAS
*Acting Director of the United States Patent and Trademark Office*